United States Patent [19]

Jackson

[11] 4,424,596
[45] Jan. 10, 1984

[54] THERAPEUTIC STOCKING STRUCTURE

[75] Inventor: Lauren M. Jackson, Yardley, Pa.

[73] Assignee: The Kendall Company, Boston, Mass.

[21] Appl. No.: 214,142

[22] Filed: Dec. 8, 1980

[51] Int. Cl.³ ............................................. A41B 11/00
[52] U.S. Cl. ......................................... 2/240; 2/409;
128/165
[58] Field of Search .................. 2/409, 240, 407, 406;
128/165

[56]  References Cited
U.S. PATENT DOCUMENTS

| 259,877 | 6/1882 | Lightcapp | 2/409 |
| 4,027,667 | 6/1977 | Swallow et al. | 2/240 |
| 4,180,869 | 1/1980 | Pedergrass et al. | 2/240 |

FOREIGN PATENT DOCUMENTS 1489842  6/1967  France .................................... 2/240

Primary Examiner—Doris L. Troutman
Attorney, Agent, or Firm—Powell L. Sprunger

[57] ABSTRACT

A therapeutic stocking structure comprising, an elongated belt having a sufficient length to encircle the waist of a wearer, with the belt having a pair of opposed sides for placement over the sides of a wearer's waist. The stocking structure has a stocking having a circumferentially elastic boot portion, and a hip panel extending upwardly from the stocking boot portion, with the hip panel having a margin at the upper end of the hip panel. The stocking margin is releasably secured to either side of the belt.

1 Claim, 2 Drawing Figures

THERAPEUTIC STOCKING STRUCTURE

BACKGROUND OF THE INVENTION

The present invention relates to elastic garments, and more particularly to therapeutic stockings.

In the recent past, therapeutic stockings have been prescribed on a relatively wide scale to prevent possible embolism in a patient. When a patient is confined to bed, for example, after an operation, the likelihood of thrombus is markedly increased due to a decrease in the velocity of blood flow in the patient's leg during confinement. Therepeutic or anti-embolism stockings cause application of a compressive pressure against the patient's leg which gradually decreases from the ankle toward the upper part of the leg. Such stockings increase the velocity of blood flow in the legs, and minimize the possibility of thromboembolism.

Anti-embolism stockings are made in assorted lengths, including those which terminate above the upper thighs of the patient, often termed thigh length stockings. A special difficulty has been encountered in the use of thigh length stockings for oversized patients, e.g. those patient's having a circumference of greater than 25 inches in the region of the upper thigh. Due to the greatly flared configuration of the upper thighs in the legs of such patients, thigh length stockings have a tendency to roll over at their tops, and then slip down the patient's legs. It is undesirable to make the stockings sufficiently tight to prevent slippage, since the stockings would restrict blood flow through the confined area and would negate the advantages sought by the stocking.

Full length stockings which are supported about the waist are proposed in U.S. Pat. No. 4,027,667, incorporated herein by reference. The disclosed stockings also exert a compressive pressure against the wearer's legs with a pressure profile generally decreasing from the ankles to the upper thighs. However, the disclosed stocking is attached about the waist by a pair of bands which renders the placement procedure on a patient unduly complicated. Also, in certain instances it is desirable to utilize only a single stocking for one leg which was not possible with the disclosed stocking.

SUMMARY OF THE INVENTION

A principal feature of the present invention is the provision of an improved therapeutic stocking structure for placement on a patient.

The stocking structure of the present invention comprises, an elongated belt having a sufficient length to encircle the waist of a wearer, with the belt having a pair of opposed sides for placement over the sides of the wearer's waist. The stocking structure has a stocking having a circumferentially elastic boot portion and hip panel extending upwardly from the stocking boot portion, with the hip panel having a margin at the upper end of the hip panel. The stocking structure has means for releasably securing the stocking margin to a side of the belt.

A feature of the present invention is that the securing means permits securement of the stocking margin to either side of the belt.

Thus, another feature of the invention is that the securing means facilitates securement of the stocking to the belt.

Yet another feature of the invention is that a pair of stockings may be readily secured to the belt on either side of the belt.

Still another feature of the invention is that the stocking structure permits securement of only one stocking to the belt to permit use of a single stocking by the patient.

Further features will become more fully apparent in the following description of the embodiments of this invention and from the appended claims.

DESCRIPTION OF THE PREFERRED EMBODIMENTS

Figure 1:
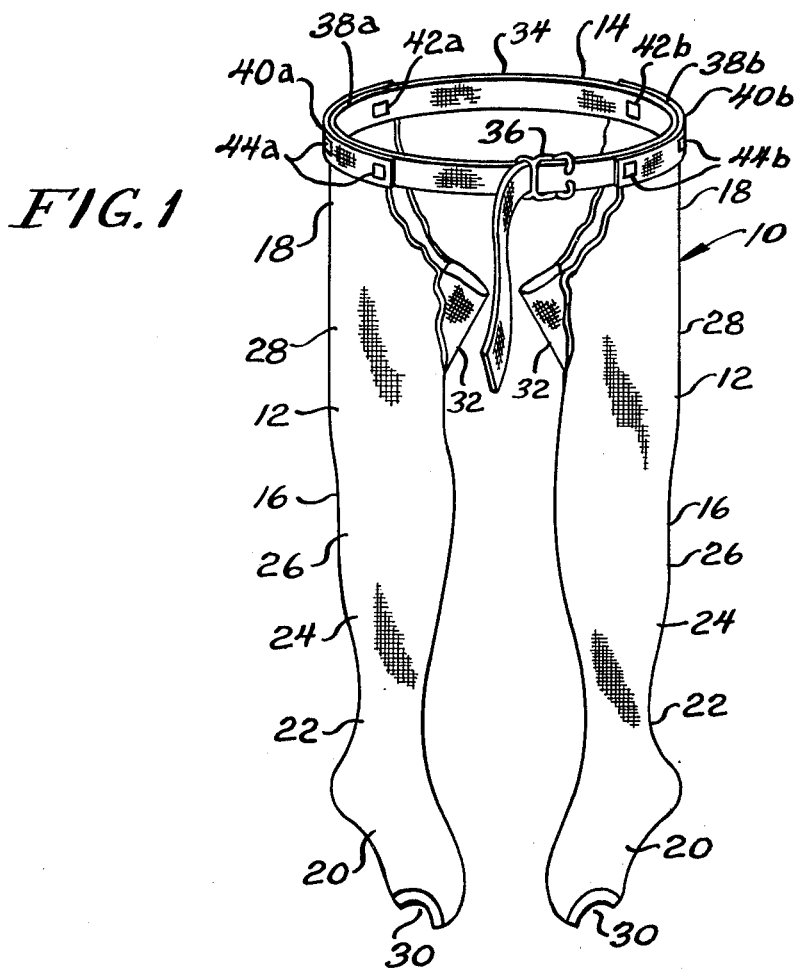
FIG. 1 is a front perspective view of a therapeutic stocking structure of the present invention.
Figure 2:
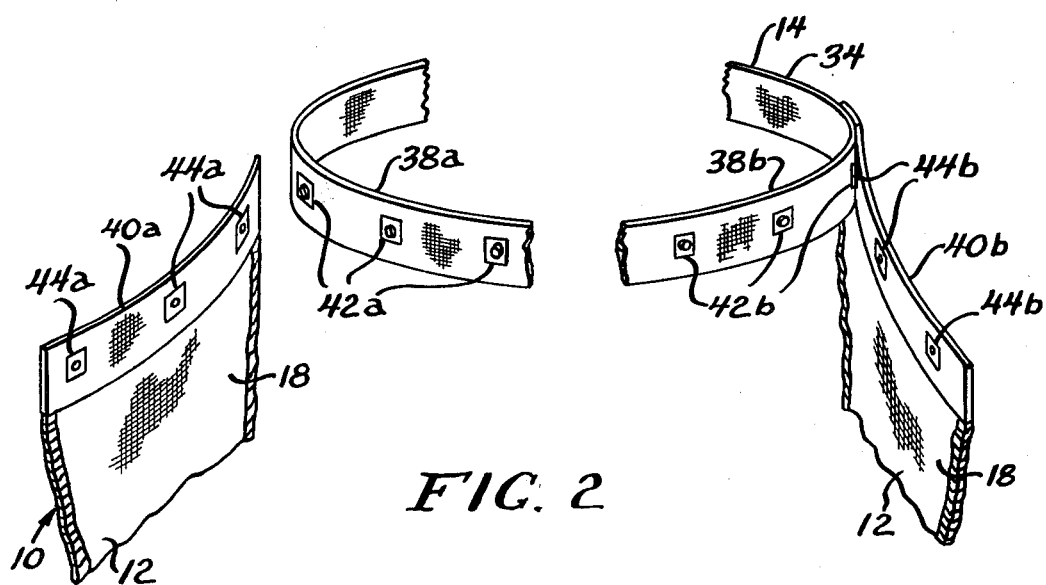
FIG. 2 is a fragmentary perspective view showing partial securement of a pair of stockings to a belt in the stocking structure.

Referring now to FIGS. 1 and 2, there is shown a therapeutic stocking structure generally designated 10 having a pair of stockings 12 and waist support means 14 for the stockings 12. The stockings 12 have a circumferentially elastic boot portion 16, and a pair of hip panels 18 extending upwardly from the boot portion 16, such that the hip panels 18 extend along the side of the hips between the waist support means 14 and the boot portion 16 when the stockings are worn. Each of the stockings 12 has a foot portion 20, an ankle portion 22, a calf portion 24, a knee portion 26, and a thigh portion 28. As shown, the foot portions 20 may have an opening 30 for inspection of the toes, and the thigh portions 28 may have a gusset 32 of circumferentially elastic fabric. The boot portions 16 exert a compressive pressure against the patient's legs to increase the velocity of blood flow in the legs and prevent possible thromboembolism in the patient. In a preferred form, the pressure profile defined by the stockings gradually decreases from the patient's ankles to the upper thighs although the compressive pressure may be reduced somewhat in the area of the knees. The boot portion 16 and hip panels 18 may be constructed in a manner as disclosed in U.S. Pat. No. 4,027,667, if desired.

The waist support means 14 comprises an elongated elastic belt 34 for placement about the waist of the patient, with the belt 34 having a buckle 36 for adjustment of the length of the belt 34 about the wearer's waist. The belt 34 has a pair of opposed side portions 38a and 38b for placement over the opposed sides of the wearer's waist. As shown, the stocking hip panels 18 have margins 40a and 40b at the upper ends of the hip panels 18, with the margins 40a and b comprising an elastic band.

The side portion 38a of the belt 34 has a plurality of spaced male snap fasteners 42a, while the side portion 38b of the belt 34 has a plurality of spaced male snap fasteners 42b. The stocking margin 40a has a plurality of female snap fasteners 44a, while the stocking margin 40b has a plurality of female snap fasteners 44b. The spacing of the male fasteners 42a and b and the female fasteners 44a and b are such that the margin 40a may be secured to either side portion 38a or 38b of the belt 34, while the margin 40b may also be secured to either side portion 38a or 38b of the belt 34.

In use, the belt 34 is first placed around the wearer's waist, and the length of the belt 34 is adjusted by the buckle 36 for the appropriate size of the wearer, Next, the stockings 12 are placed upon the wearer's legs, and the stocking margins 40a and 40b of the stockings 12 are secured to the side portions 38a and 38b of the belt 34. Since the stocking margins 40a and 40b may be secured to either side portion 38a or 38b of the belt 34, the stocking structure 10 greatly facilitates attachment of the stockings to the waist support means 14. When it is desired to remove the stockings 12 from the patient, the upper margins 40a and 40b of the stockings 12 may be removed from the belt side portions 38a and 38b. It will be apparent that the stocking structure 10 permits securement of either one stocking margin 40a or 40b to the belt side portions 38a or 38b, or permits securement of the upper margins 40a and 40b of both stockings 12 to the belt 34. Thus, the stocking structure 10 permits the use of one or two stockings on the patient's legs, as desired.

The foregoing detailed description is given for clearness of understanding only, and no unnecessary limitations should be understood therefrom, as modifications will be obvious to those skilled in the art.

I claim:

1. A therapeutic stocking structure having interchangeable components including a waist belt totally encircling the body and two stockings releasably secured to said belt at side portions thereof, either of said stockings being releasably secured to either of said belt side portions and either or both of said stockings being worn by a wearer for therapeutic purposes, said belt comprising an extended length band of material and having means for adjusting the length of said belt about a wearer's waist, each of said pair of stockings comprising a circumferential, elastic boot portion, a hip panel extending upwardly from said elastic boot portion, and a stocking margin band at the upper end of said hip panel, there being means for releasably securing said band to either side portion of said waist encircling belt, on the outer surface thereof, including identical, first quick disconnect means on either side portion of said waist encircling belt and second, mating quick disconnect means on each of said stocking margin bands, on an inner surface thereof, facing a wearer, whereby in use, one or both of said stockings may be worn with the stocking margin bands thereof being releasably secured to either of said side portions of said belt.

* * * * *